United States Patent
Schmidt et al.

[19]

[11] Patent Number: 6,071,526
[45] Date of Patent: Jun. 6, 2000

[54] COSMETIC OR COSMETIC PRODUCT FOR FIRMING AND SOOTHING THE SKIN IN PARTICULAR IN THE CASE OF CELLULITE

[75] Inventors: Alfred Schmidt, Hamburg; Heinrich Wieland, St. Peter, both of Germany

[73] Assignee: S.W. Patentverwertungs Ges m.b. H., Germany

[21] Appl. No.: 09/256,854

[22] Filed: Feb. 24, 1999

Related U.S. Application Data

[62] Division of application No. 08/825,105, Mar. 27, 1997, Pat. No. 5,945,109.

[51] Int. Cl.[7] ....................................................... A61K 7/00
[52] U.S. Cl. ............................................................ 424/401
[58] Field of Search ............................................... 424/401

[56] References Cited

U.S. PATENT DOCUMENTS

| 4,895,715 | 1/1990 | Neri et al. | 424/10 |
|---|---|---|---|
| 4,937,250 | 6/1990 | Bowman et al. | 514/341 |
| 5,614,215 | 3/1997 | Ribier et al. | 424/450 |

FOREIGN PATENT DOCUMENTS

| 9736570 | 10/1997 | European Pat. Off. . |
| 9917712 | 4/1999 | European Pat. Off. . |

OTHER PUBLICATIONS

BRODIE A.M.H.: "Aromatase Inhibition and Its Pharmacologic Implications", Biochemical Pharmacology, (1985) 34/18 (3213–3219). CODEN: BCPCA6, XP002101635 United Kingdom.

*Primary Examiner*—James M. Spear
*Attorney, Agent, or Firm*—Ostrolenk, Faber, Gerb & Soffen, LLP

[57] ABSTRACT

The invention discloses a cosmetic product for topical administration in disturbed subcutaneous connective fatty tissue, in particular cellulite, where one or more substance(s) present in the product locally inhibit(s) the formation and/or action of estrogens in the subcutaneous fatty tissue. Suitable substances are, in particular, aromatase inhibitors and/or anti-estrogens. The cosmetic is effective in the cosmetic treatment of cellulite.

7 Claims, 2 Drawing Sheets

COSMETIC OR COSMETIC PRODUCT FOR FIRMING AND SOOTHING THE SKIN IN PARTICULAR IN THE CASE OF CELLULITE

This is a divisional of application Ser. No. 08/825,105, filed Mar. 27, 1997 U.S. Pat. No. 5,945,109.

DESCRIPTION

The present invention relates to a cosmetic, or cosmetic product, for firming and smoothing the skin, in particular in the case of cellulite, the cosmetic, or cosmetic product, being applied topically.

Ways and means of firming and smoothing the skin are an important cosmetic challenge. An undesirable consequence of the formation of fatty tissue in the skin is, in particular, cellulite.

Cellulite is a term for non-inflammatory constitutional (gender-typical) adiposis with mild lymphatic blockade and mild (mucoid) formation of edema in the connective tissue zone (so-called Adipositas circumscripta oedematosa). Cellulite is found in particular in women in the hip, thigh and gluteal region. In most cases, a so-called "quilt syndrome" (connective tissue septation resulting in reticulate dimpling of the surface) and the so-called "orange-peel skin syndrome" (infundibuliform follicular retractions after squeezing). This results in connective tissue disorder of the subcutis and an increase in the bulk of lipids in the fat cavities. However, cellulite symptoms are not pathological.

An overview of definition, symptoms and therapeutic attempts is found in the paper by M. Rimpler in: "Biologische Medizin", year 23, Issue 5, pages 284–286 (1994). A reduced function of the vascular system, which represents major damage, is held responsible for the occurrence of cellulite. The proposed treatments are based on the finding that microcirculatory disorders in the dermal layer in the cellulite stage adversely affect all metabolic processes and synthetic performances of subsequent cell populations, especially those of the fibroplasts in the corium and of the epidermal cells. Accordingly, the aim of any treatment must be to reconstitute sufficient vascularization of, and supply to, the subcutis. To this end a massage system was developed where physical treatment of the skin surface with the aid of a small massage device is combined with the use of selected plant extracts (see M. Rimpler, "Die Dermapunkturfibel" [Dermapuncture book], 1st Edition, pp. 93–126, G. A. Ulmer Verlag, Tuningen (1993); Cellulite study, Syllabus No. 1990-2, MHH OE 4330, Medical College Hanover (1990); and M. Rimpler, Chr. Rimpler and S. Lemke in: "Haut", Issue 3 (1994), pages 1–4.

An alternative attempt at combining mechanical and drug action on the skin regions affected by cellulite is disclosed in U.S. Pat. No. 4,829,987. The respective parts of the body, in particular thighs, hips and buttocks, are subjected to a dynamic isometric action for which specific exercise equipment is used, while these parts of the body are provided with a bandage soaked in a solution of a mineral substance, for example sea mud. This treatment is intended to extract certain minerals from the fatty deposits of the body in order to revitalize the elastin of the soft tissue.

The disadvantage of such mechanical treatment methods is that external pressure caused by vigorous massaging irritates the cells and causes a multiplicity of reactions in the dermal cells. As a result, the cells produce more elastase and collagenase. These enzymes, which degrade connective tissue, tend to make the connective tissue go limp rather than firming it.

Besides massage systems, there have recently been marketed cosmetics which comprise active ingredients claimed to be effective against cellulite such as, for example, seaweed extract, caffeine, theophylline or lipid-degrading enzymes. Another cream against cellulite comprises, as active ingredients, extracts of Elizabethae, a coral species and of heather, it being intended for these active ingredients to combat inflammation in the tissue and thus the formation of tissue-weakening enzymes, in addition to an algal constituent intended to active lipid oxidation; in addition, Centella asiatica, milk proteins and vitamin A are intended to promote the weakened collagen and elastin production, and fruit acids are intended to smooth the skin.

However, all methods for treating cellulite which have been available to date are not satisfactory.

It is therefore the object of the present invention locally to improve the cellulite-typical, disturbed structure of the subcutaneous connective fatty tissue and thus again to firm and smooth the skin.

The object is achieved by a cosmetic product which comprises one or more substance(s) which inhibit(s) the formation and/or the action of estrogens for topical administration in cases of disorders of the subcutaneous connective fatty tissue, in particular in cases of cellulite.

The present invention furthermore relates to the use of the above-mentioned substance(s) as cosmetic for local topical administration in the case of disorders of the subcutaneous connective fatty tissue, in particular in cases of cellulite, and to the method for the cosmetic treatment of cellulite in which an above-mentioned cosmetic product is applied to the skin to be treated.

Figure 1:
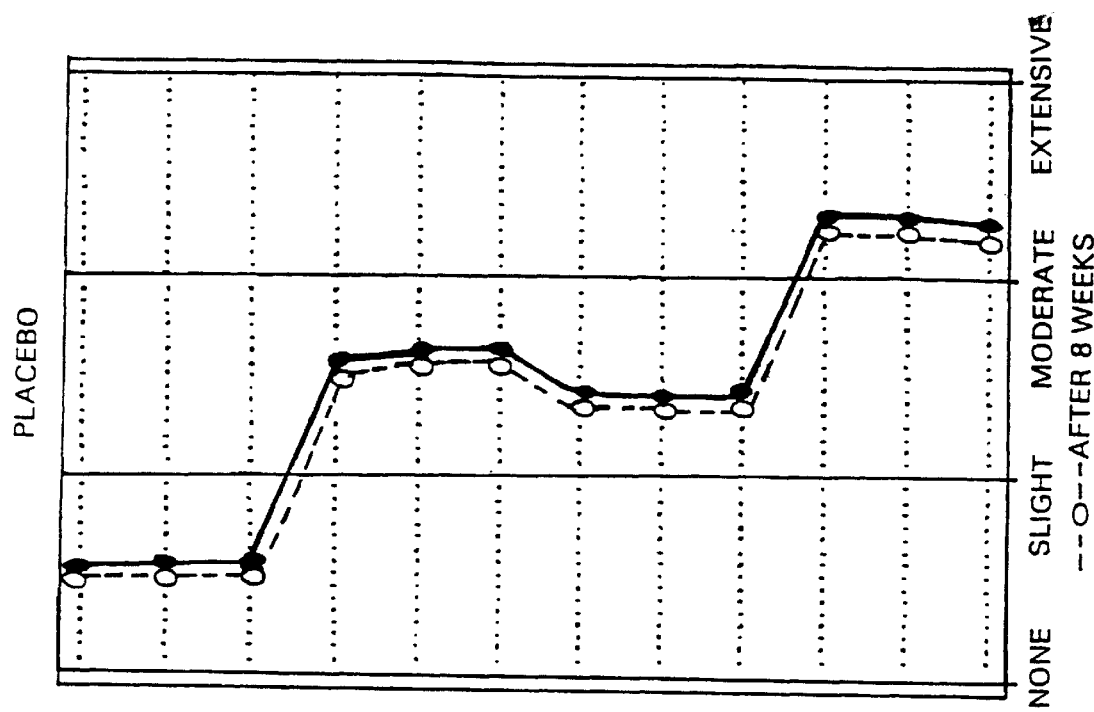
FIGS. 1 and 2 show the efficacy of the composition according to the invention in reducing cellulite in comparison with a placebo, FIG. 1 showing the profile of all assessment criteria and FIG. 2 showing the total score in the problem zones thigh/buttocks.
Figure 1:
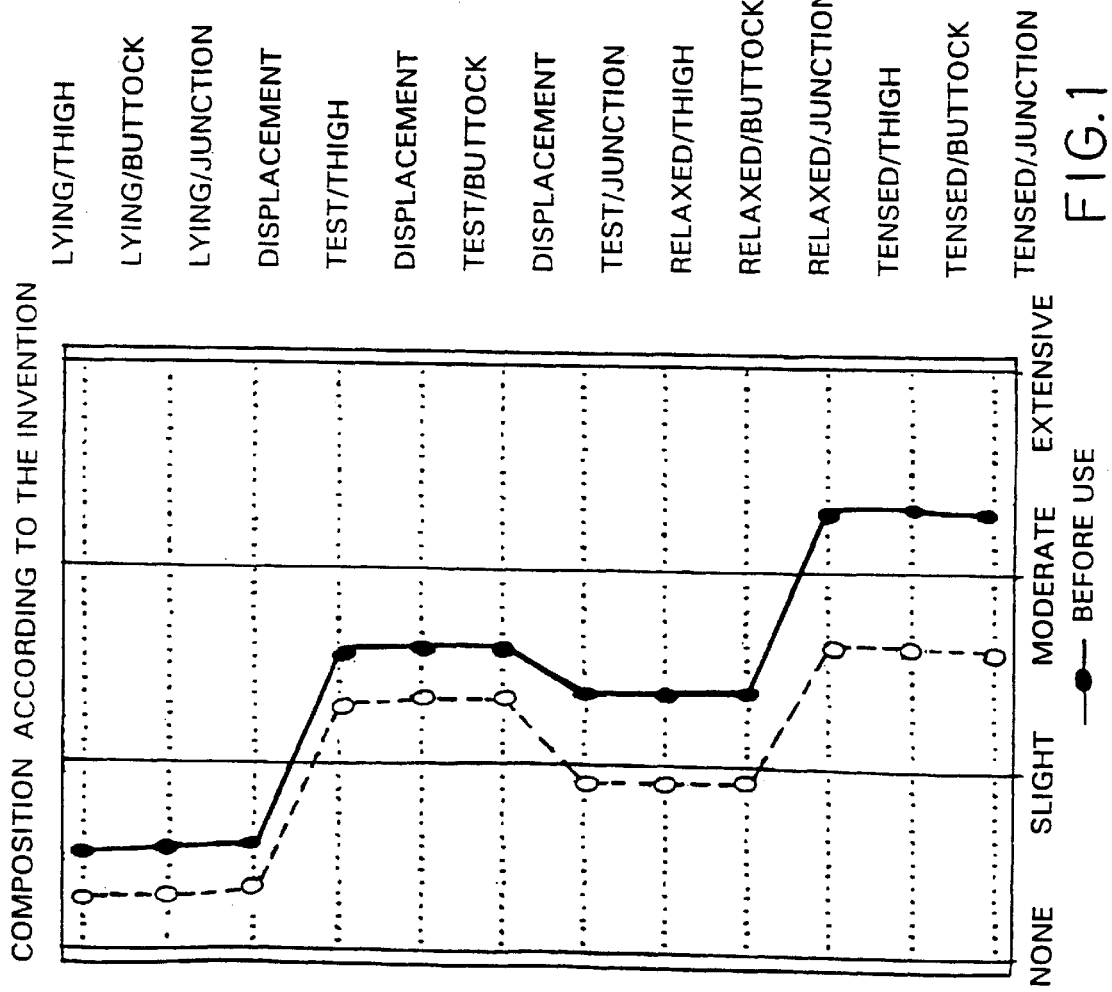

After application, the cosmetic product, or the cosmetic, inhibits the formation and/or action of estrogens in the subcutaneous fatty tissue (subcutis). When used locally/topically, i.e. administration of the cosmetic product, or the above-mentioned cosmetic, to the skin with the fatty tissue, suppression of the formation and/or action of the estrogens in the subcutaneous fatty tissue is achieved. This allows an advantageous restructuring process of the scleroproteins with reticulation of the connective tissue filaments to be achieved. In the target group of women, this restructuring process causes in the "female" type of the subcutaneous connective tissue structure (where connective tissue filaments extend straight downwards from the dermis so that the fatty tissue in the subcutis is subdivided into roughly columnar chambers) the tendency to form the "male" type of the subcutaneous connective tissue structure. As a result, the connective tissue paths in the subcutis are markedly shallower and reticulated to a higher degree than previously, so that a large number of smaller "fat cavities" are formed. The tensile and compressive forces which act on the skin are therefore distributed in markedly greater zones in accordance with the laws of physics (parallelogram of forces) than prior to application of the above-mentioned substance. Due to the restructuring process, dimples or irregular surfaces, as can be described by the "quilt syndrome" or "orange peel skin syndrome", are observed to a lesser extent, or not at all, after use. The cosmetic effect is based on the retarded and reduced replenishment and de novo formation of adipose cells while retaining the physiological cell metabolism in the fatty tissue. This also results in a lower degree of replenishment in the existing adipose cells of the subcutaneous fatty tissue. In consequence, this "spasmolysis" of the fatty tissue results in an improvement in the disturbed local blood circulation and in the inhibited transport of lymph and edema.

Consistent local and topical administration (for example 1–2xper day) to the cosmetic problem zones results in action beginning and thus in rearrangement of the connective tissue structures of the subcutaneous fatty tissue within as little as a few weeks.

The advantages of the present invention are discernable in particular in the case of cellulite. During use of the cosmetic product, or of the cosmetic, which inhibits formation and/or action of estrogens in the treated cutaneous fatty tissue zones, the skin surface becomes increasingly smooth and firm, while the undesirable "quilt syndrome" declines constantly. This can be observed mainly in the hip, buttock and thigh zone (problem zone) of females.

To achieve the above-described desired topical effect, the cosmetic product, or cosmetic, must comprise one or more substances which cause the underlying inhibition of formation and/or action of estrogens in the subcutaneous fatty tissue, estrogens being understood as meaning all natural, female sexual hormones with estrogen action.

With respect to substances which inhibit the formation and/or action of estrogens, two classes of substances are suitable, in particular, in accordance with the present invention, and these shall be described in greater detail in the following text.

On the one hand, they are substances which reduce the estrogen content by inhibiting estrogen biosynthesis. Since aromatase is a key enzyme in the biosynthetic pathway of estrogen, substances which are particularly suitable for this purpose are steroid-type and non-steroid-type aromatase inhibitors.

On the other hand, such substances are anti-estrogens, i.e. those substances which block estrogen receptors and thus inhibit the action of estrogens by way of being antagonists.

Preferred substances which are added in accordance with the invention to the cosmetic to be used are those of the aromatase inhibitors. It is assumed that the aromatase inhibitors inhibit local de novo formation of estrogens in the relevant fatty tissue and thus efficiently affect the cosmetically advantageous restructuring process of the connective tissue structures of the subcutaneous fatty tissue as described above and so counteracts, for example, cellulite.

Examples of aromatase inhibitors are the substances 4-hydroxyandrost-4-ene-3,17-dione (Formestan™), 6-methylene-androstra-1,4-diene-3,17-dione (Exemestan™), 10-(2-propynyl)estr-4-ene-3,17-dione (MDL 18962) and 7α-substituted androstenedione derivatives as examples of steroid-type aromatase inhibitors, and also imidazole and triazole derivatives as examples of non-steroid-type aromatase inhibitors, such as 6-[(4-chlorophenyl)(1H-1,2,4-triazole-1-yl)-methyl]-1-methyl-1H-benzotriazole (Vorazol™), 2,2'-[5-(1H-1,2,4-triazole-1-yl-methyl)-1,3-phenylene]bis(2-methyl-proprionitrile) (Arimidex™), 4-[1-(cyanophenyl)-1-(1,2,4-triazolyl) methyl]benzonitrile] (Letrozol™), (4-(5,6,7,8-tetrahydroimidazo-[1,5a]-pyridin-5-yl)benzonitrile monohydrochloride (Fadrozol™) and pyridoglutethimide (Rogletimid™).

With regard to the terminology of these substances and their availability, see, for example, "Rote Liste", Editio Cantor, Aulendorf (DE), (1985).

Such aromatase inhibitors are known per se, but in an entirely different field, namely as systemically applied active ingredients for the medical/therapeutic treatment of breast cancer. Reference is made in this context to the review articles by A. M. H. Brodi in: "J. Steorid Biochem. Molec. Biol.", Vol. 49, No. 4–6, pp. 281–287 (1994), and P. E. Goss and K. M. E. H. Gwyn in: "Journal of Clinical Oncology", Vol. 12, No. 11, pp. 2460–2470 (1994). With regard to the classification of the aromatase inhibitors and the subsequent reduction in estrogen, reference is made to the further references given in the above-mentioned review articles, see, for example, A. M. H. Brodi et al. in: "J. Steroid Biochem. Molec. Biol.", Vol. 7, pp. 787–793 (1976), and D. A. Marsh et al. in: "J. Med. Chem.", Vol. 28, pp. 788–795 (1985).

Specific azoie derivatives and their aromatase-inhibitory and antimycotic action are furthermore described in EP-A-0 575 210.

Surprisingly, it has emerged that soya glycins (INCI name in accordance with Linné's system) contain substances with aromatase-inhibitory properties, and that these aromatase inhibitors originating from soya glycins can be employed within the scope of the present invention. These aromatase inhibitors originating from soya glycins can be obtained readily by providing "Glycine soja" (soybean oil or soybean extract or sojasterol) and subsequently isolating the aromatase-inhibitory component by customary separation methods, such as liquid chromatography, in particular by means of HPLC.

Furthermore, it has emerged that the aromatase-inhibitory action of the soya glycins can be increased by subjecting the soya glycins to oxidative treatment.

This oxidized form originating from soya glycins is synthesized in a simple manner by oxidizing the soya glycins (soybean oil or soybean extract or sojasterol) and subsequently isolating the aromatase-inhibitory component by customary separation methods, such as liquid chromatography, in particular by means of HPLC.

The oxidation can be affected enzymatically, for example, in accordance with the method described by Y. Fujimoto et al: in: "J. Am. Chem. Soc.", Vol. 104, pp. 4718–4720 (1982), or chemically, for example, in accordance with the method described by P. Welzel in: "Tetrahedron", Vol. 41, No. 20, pp. 4509–4517 (1985).

Examples of substances from the class of the anti-estrogens which are to be mentioned are, in particular, the non-steroid-type estrogen antagonists tamoxifen (Z-2-[4-(1, 2-diphenyl-1-butenyl)-phenoxy]-N,N-dimethylamine) and aminoglutethimide (3-(4-aminophenyl)-3-ethyl-2,6-piperidine-dione) and the analogs and derivatives of these, for example 3-hydroxytamoxifen, 1-hydroxytamoxifen and the 7-α-alkylsulfinyltamoxifen analog (ICI 182, 780).

With regard to the terminology of these substances and their availability see, for example, "Rote Liste", Editio Cantor, Aulendorf (DE), (1985).

Again, these anti-estrogens have previously been described only in connection with the systemic-therapeutic treatment of breast cancer.

The reason for the action of steroid-type and non-steroid-type aromatase inhibitors and of anti-estrogens for the use according to the invention in the case of cellulite is assumed to be that local inhibition of aromatase, i.e. inhibition of the formation of estrogen in situ, or anti-estrogen action, results in a permanently reduced estrogen content in the subcutaneous lipid cells. Thus, in accordance with the present invention, local flooding with the topically applied active ingredient inhibits in fact only the formation or action of estrogen in the peripheral subcutaneous fatty tissue. An androgen action was not to be expected, nor was it detected. The substances employed in accordance with the invention act only locally, i.e. not systemically. No intolerance was observed in any of the treated females.

To allow the mechanisms of action for solving the cosmetic problems to mutually complement and advantageously affect each other, a preferred embodiment is the use of a cosmetic for dermal administration with a combination of one or more aromatase inhibitors and one or more anti-estrogens. The ratio weight to be used in the combination is not critical and can be adapted to suit the specific requirements. Thus, for example, either the one type of substance or the other type of substance may prevail, depending on which route of action is emphasized. The weight ratio of aromatase inhibitor to anti-estrogen is, for example, in a range of from 90/10 to 10/90, in particular in a range of from 60/40 to 40/60.

Another reason why the cosmetic product according to the invention, or the cosmetic according to the invention, with the estrogen-inhibitory active ingredients is very well suited to topical administration is because the active ingredients which are possible are, as a rule, readily, or even very readily absorbed percutaneously. If percutaneous absorption causes problems in individual cases, or if an increased percutaneous absorption is to be achieved, agents for promoting percutaneous absorption can additionally preferably be employed in the cosmetic to be used. Such agents for promoting percutaneous absorption are known. Examples which are suitable are hyaluronidates, dimethyl sulfoxide (DMSO) and the like.

For topical application, a formulation of the substance to be used which is suitable for this purpose may be selected, e.g. an ointment, a cream, a gel, an emulsion (lotion), a powder or an oil and the like. To this end, the cosmetic product, or the cosmetic, comprises additives which are customary for the relevant formulation as an ointment, cream, gel, emulsion or oil. Described and commercially available, conventional skincare agents are thoroughly suitable in the respective formulations for use in the present invention. Substances which act as examples of customary additives for such formulations are vegetable oils such as almond oil, olive oil, peach kernel oil, groundnut oil, castor oil and the like, plant extracts, essential oils, vitamin oils, fats and fat-like substances, lipoids, phosphatides, hydrocarbons such as paraffins, petroleum jelly, lanolin, waxes and the like, detergents, other skin-active substances such as lecithin, lanolin alcohols, carotin and the like, skin nutrients, perfumes, alcohols, glycerol, glycols, urea, talc, preservatives, sunscreens, colors such as titanium white and zinc white, antioxidants and the like. The base used is generally water, thus resulting—normally with an addition of emulsifiers such as fatty alcohol sulfates, alkali metal soaps, lecithins, triethanolamine and the like—in an O/W or W/O emulsion.

The concentrations of the active substance for inhibiting estrogen formation, or estrogen action, in such formulations are not critical and can be adapted to suit the application in question. A suitable example is an active ingredient concentration in the entire cosmetic product of 0.0001 to 10 percent by weight (% by weight), preferably 0.001 to 1% by weight and in particular 0.01 to 0.5% by weight.

The content of the resorption promoter to be employed if appropriate depends mainly on the nature of the resorption promoter. The amounts usually employed in each case are entirely suitable. Hyaluronidates, for example, can be used in a concentration of 0.01 to 1% by weight, in particular 0.05 to 0.2% by weight. In the case of DMSO, a wider range is suitable, for example 1 to 25% by weight, in particular 5 to 10% by weight.

The other additives which are present, if appropriate, can be employed in those amounts which are customary for the formulations in question.

For the cosmetic treatment of disorders of the female subcutaneous fatty tissue, in particular for the cosmetic treatment of cellulite forms, it suffices regularly to apply the above-described cosmetic, or the cosmetic product, to the skin zones to be treated, in particular in the region of the hips, thighs and buttocks, and to be massaged in gently (for example once to twice per day). The treatment method according to the invention results in smoothing and firming of the skin after as little as a few weeks, without it being possible for systemic side effects to occur, or without systemic side effects occurring.

Accordingly, the cosmetic treatment method according to the present invention guarantees an efficient cosmetic activity without requiring complicated mechanical treatment, such as is required in the mechanical treatment methods for cellulite which are described at the outset. In contrast to dermal cellulite products which have recently appeared on the market and are criticized in this respect, the cosmetic according to the invention has an outstanding activity against cellulite.

The present invention is illustrated in greater detail hereinbelow with the aid of the examples which follow.

EXAMPLE 1

The following constituents were mixed together to prepare a cream:

| | |
|---|---|
| Urea | 10.0 g |
| Titanium oxide | 15.0 g |
| Petroleum jelly | 25.0 g |
| Isopropyl palmitate | 10.0 g |
| Hardened groundnut oil | 10.0 g |
| Tween 80 | 5.0 g |
| Oxidized soya glycins with aromatase-inhibitory action | 0.35 g |
| Purified water to | 100.0 g |

Clinical Test of the Efficacy of the Anti-cellulite Cream According to the Invention Test design. The effect of the above cream on the level of the orange-peel skin syndrome in female volunteers (24 women aged 20 to 62 years) with cellulite in stage II–III was tested within the scope of a randomized double-blind clinical study in comparison with placebo. The placebo used was the cream base without active substance. The study was carried out as a half-sided experiment, i.e. each volunteer treated one side of the body with the cream product according to the invention and the second side of the body with placebo. The allocation of the two treatments to the right-hand or left-hand side of the body was carried out with the aid of a randomization list prepared prior to the beginning of the study. Over the entire course of the study, both creams were applied once daily to the affected regions of the body and massaged in gently. The amount to be applied was decided by the test subjects according to their own subjective feeling. After the initial examination, two control examinations were carried out in the course of the treatment at four-week intervals. Prior to the beginning of the treatment, an extensive case history was recorded with regard to possible cellulite-affecting parameters, in addition to assessing the cellulite.

Assessment criteria. To classify the cellulite, the macroscopic appearance of the skin in the three problem zones thighs, buttocks and transitional zone thighs/buttocks was assessed with the aid of a pre-defined, four-step scale in which the figures denote: 0=no orange skin and 1=slight, 2=moderate, 3=pronounced orange skin syndrome. The assessment was carried out both when lying down and when standing up on relaxed and tensed muscles. Furthermore, whether, and to what degree, it was possible to trigger the orange skin syndrome by pushing the skin together was tested. In this way, a total of 12 observation values were recorded for the side of the body which was treated with the product according to the invention and for the side which was treated with the placebo. To test for efficacy, an overall score was formed as the total of all 12 observation values.

Results. In the initial examination, no differences were observed with regard to the level of cellulite between the side of the body which had been treated in accordance with the invention and the side which had been treated with placebo. The cellulite-typical symptoms were most pronounced when standing up and with tensed muscles. FIG. 1 shows the mean values for the assessment when lying down, when standing up with relaxed and with tensed muscles, and for the pushing-together test for each of the three problem zones of a profile graph over all variables in the course of the treatment. The left-hand-side graph shows the profile for the treatment according to the invention, while the right-hand-side graph shows the profile for the placebo treatment with in each case one curve for the initial examination and the second control examination. The curve for the second control examination of the side of the body which had been treated in accordance with the invention is markedly shifted towards the left into the lower value range, while the two curves for the placebo-treated side of the body are virtually congruent.

Figure 2:
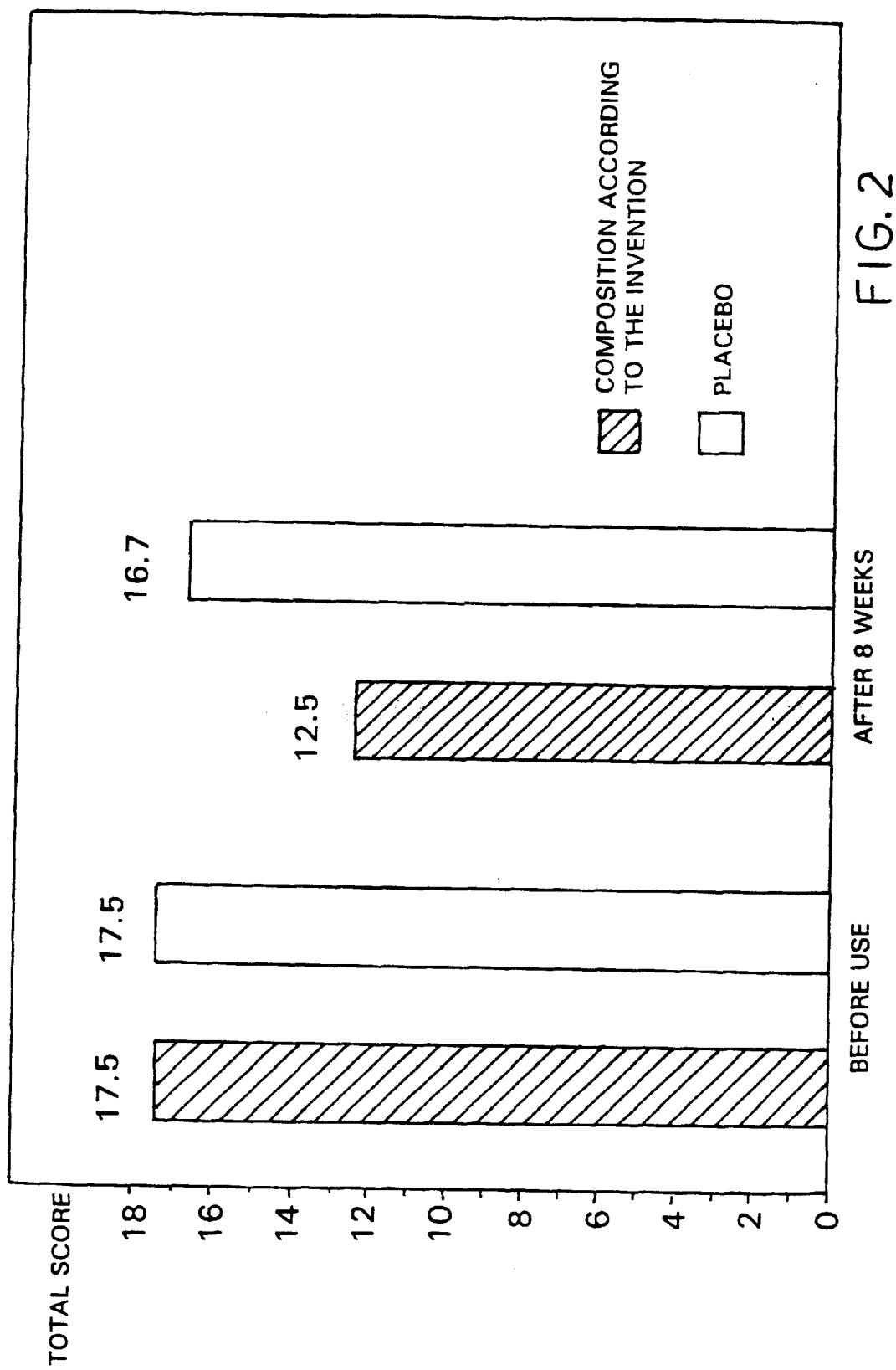

Demonstration of efficacy. The examination of the efficacy of the cream product according to the invention is based on the reduction of the overall score, i.e. the difference between overall score at the beginning of the treatment and overall score in the second control examination. The expected values of the two treatment groups were calculated by analysis of the variance following the method of least squares and show a clear (highly significant p<0.001) superiority of the cream according to the invention (see FIG. 2).

Acceptability. In none of the volunteers was a deterioration of the appearance of the skin observed on either of the two sides of the body in the course of the study. No clinical abnormalities, which could be the result of an allergic reaction in the treated regions of the body, were found during the treatment within the scope of the study.

EXAMPLE 2

The following components were mixed to prepare a gel:

| | |
|---|---|
| Ethanol 90% | 7.0 g |
| Carbopol 934P | 0.7 g |
| Triethanolamine | 0.2 g |
| Polysorbate 80 | 5.0 g |
| Glycerol | 3.0 g |
| Oxidized soya glycins with aromatase-inhibitory action | 0.35 g |
| Purified water to | 100.0 g |

The gel was applied twice daily (mornings and evenings) to the thighs and buttocks of a volunteer who had cellulite and exhibited a "quilt syndrome" when standing up and was massaged in gently.

After a treatment period of six weeks, the skin surface in the zones which had received applications was of smooth appearance and the "quilt syndrome" was markedly less pronounced.

EXAMPLE 3

The following constituents were mixed together to prepare a cream:

| | |
|---|---|
| Propylene glycol | 25.0 g |
| Isopropyl myristate | 6.0 g |
| Sorbitan monostearate | 1.0 g |
| Polysorbate 80 | 2.0 g |
| Cetylstearyl alcohol | 6.0 g |
| Stearyl alcohol | 2.0 g |
| Glycerol monostearate | 1.0 g |
| Hyaluronic acid | 0.1 g |
| Oxidized soya glycins with aromatase-inhibitory action | 0.35 g |
| Purified water to. | 100.0 g |

The cream was applied twice daily (mornings and evenings) to the thighs and buttocks of a volunteer who had cellulite and exhibited a "quilt syndrome" when standing up and was massaged in gently.

After a treatment which extended over four weeks, the treated skin surface was of smooth and firm appearance. Cellulite symptoms were significantly reduced.

EXAMPLE 4

A cream was prepared in accordance with Example 1 and applied, but with the difference that 1 mg of 4-hydroxytamoxifen was employed instead of 0.35 g of oxidized soya glycins with aromatase-inhibitory action. After the treatment, which extended over six weeks, the treated surface was smooth and firm. Signs of "quilt syndrome" were greatly reduced.

EXAMPLE 5

A cream was prepared in accordance with Example 1 and applied, but with the difference that 0.025 g of 4-hydroxytamoxifen was employed instead of 0.35 g of oxidized soya glycins with aromatase-inhibitory action.

The cellulite syndrome on the treated skin surfaces was greatly reduced after a treatment of only four weeks.

We claim:

1. A method of treating cellulite comprising locally and topically applying to skin a substance which inhibits the formation and/or action of estrogens thereby improving subcutaneous connective fatty tissue disturbances.

2. The method of claim 1, wherein the substance is selected from the group consisting of aromatase inhibitors and anti-estrogens.

3. The method of claim 1, wherein the substance is an aromatase inhibitor.

4. The method of claim 1, wherein the substance originates from soya glycins.

5. The method of claim 4, wherein the substance from soya glycins has been subjected to oxidative treatment.

6. The method of claim 2, wherein the substance is applied to a skin showing cellulite.

7. A method for the cosmetic treatment of cellulite in which a cosmetic product comprising a substance which inhibits the formation or action of estrogens is applied to the skin to be treated.

* * * * *